United States Patent [19]

McCusker et al.

[11] 4,413,510
[45] Nov. 8, 1983

[54] COATING ADHESION TESTING

[75] Inventors: Joseph H. McCusker, Princeton; Barry J. Thaler, Plainsboro; Wei H. Tsien, Cherry Hill, all of N.J.

[73] Assignee: RCA Corporation, New York, N.Y.

[21] Appl. No.: 323,057

[22] Filed: Nov. 19, 1981

[51] Int. Cl.³ .......................................... G01N 19/04
[52] U.S. Cl. ................................................. 73/150 A
[58] Field of Search ...................... 73/150 A, 789, 790, 73/791, 792, 793, 827

[56] References Cited

U.S. PATENT DOCUMENTS 1,653,714 12/1927 Lewis et al. ....................... 73/793 X
2,853,875 9/1958 Alderuccio et al. .................. 73/150

OTHER PUBLICATIONS

Engel, P. A. et al., Coating Bond Strength Test Method, IBM Technical Disclosure Bulletin, vol. 20, No. 11A (4/78).

Primary Examiner—Jerry W. Myracle
Attorney, Agent, or Firm—Birgit E. Morris

[57] ABSTRACT

A method of testing the adhesion between a coating and its substrate applies a force to a sample by means of a plunger and supporting ring apparatus. The force is increased laterally while the force and the resulting deflection are measured. When the slope of the force-deflection curve changes abruptly, the test is terminated, and the value of force required to produce that condition is noted. The test is nondestructive.

3 Claims, 3 Drawing Figures

COATING ADHESION TESTING

BACKGROUND OF THE INVENTION

This invention is in the field of adhesion testing. In particular, this invention relates to a method of testing the adhesion characteristics of coatings and for providing a pass-fail test for use in the manufacture of coated substrates.

DESCRIPTION OF THE PRIOR ART

The degree of adhesion between a coating and the substrate upon which the coating is placed must often be determined at some point in a manufacturing cycle. For example, the adhesion between a glass-like material and a substrate is of importance in a porcelain-on-steel printed circuit board. Depending upon the manufacturing processes of the printed circuit board, the adhesion characteristics between the porcelain and the steel must be known with a reasonable degree of certainty. Further, the adhesion for boards which are expected to undergo many high temperature firings may have to be higher than those of boards which are fired only once.

The adhesion between a coating and its substrate has been measured in various ways. For example, paint coatings are often evaluated by a so-called scratch test. A calibrated scratching tool is applied to a test sample. A high quality adhesion between the paint and the substrate prevents the penetration of the scratching tool and the workpiece passes. If the adhesion is low, however, the tool can penetrate and scratch the coating, in which case the sample fails.

In adhesion testing where the material of the coating is relatively hard, pull tests are employed. A pulling apparatus having calibrated force and deflection gauges is attached to the coating. The substrate is then held statically and force is applied in a gradually increasing manner until the coating separates from the substrate, whereupon the degree of force required to cause the separation is recorded.

Heretofore, most of the adhesion testing methods have been somewhat, if not totally, destructive. The scratch test for paint produces damage of some kind in most coatings. The pull test for adhesion, because it results in the separation of the coating from the substrate, is also destructive. This is a need in the art for a nondestructive method of testing the adhesive qualities of coatings on substrates.

SUMMARY OF THE INVENTION

The present method, which is applicable to relatively hard materials on substrates of another material, applies a force to a sample by means of a plunger and supporting ring apparatus. The force is increased gradually while the force and the resulting deflection are measured. At some value of the applied force, the slope of the force-deflection curve changes abruptly. At that point, if the coating is of a glass-like material, it may or may not have cracked. Whether or not a crack does appear in the material at that point is not meaningful for compressively prestressed coatings, however, because any such crack will not propagate throughout the material under most circumstances. The test is completed and is stopped when the slope change occurs.

A plurality of workpieces is put through the apparatus to determine the limits of the adhesion values in a given batch. Once those limits have been determined, an engineer may select a value of force below which the adhesion is insufficient for satisfactory quality of the end product and above which it is sufficient. This information may be used thereafter by a human tester, who can set a pass-fail limit on a testing apparatus similar to that used in the initial determination of the limits and test a plurality of samples to determine which of them have adhesion above the preselected value. As an alternative to human testing, the information which is determined in the initial evaluation can be used to preset the pass-fail mechanism of an automatic tester. In either case, the quality of the product resulting from the present testing method will be higher than the quality of product which would be obtained if the method were not applied.

DESCRIPTION OF THE PREFERRED EMBODIMENT

Figure 1:
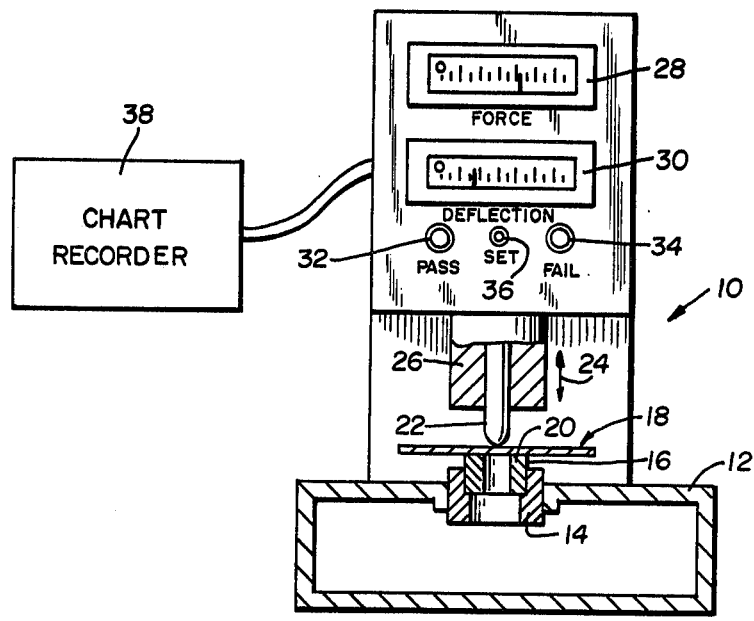
FIG. 1 shows, in partial section, an apparatus useful in the practice of the present method.

The present method can be carried out in apparatus 10 of the kind shown in FIG. 1. This apparatus 10 is diagrammatically representative of apparatus which is presently commercially available from several manufacturers. The apparatus 10 has a base 12, which carries a support 14 for a replaceable supporting ring 16. A workpiece 18 may be supported against motion in a given direction, downward as shown, on the annular upper surface 20 of the ring 16.

A force applying member, e.g., a plunger 22, which is moveable in the direction of the arrows 24 in FIG. 1 in a support sleeve 26, contacts the surface of the coated workpiece 18. A mechanism, not shown, is provided to bias the plunger 22 against the surface of the coating on the workpiece 18 and to increase the force in a controlled and uniform manner. Scales 28 and 30, which are indicative of the force and the deflection at any given instant of time, are provided on the apparatus.

Optionally, and if the apparatus is to be used in a factory environment by a human tester, the apparatus also includes pass and fail indicator lights 32 and 34. A setting knob 36 is provided to calibrate the apparatus to a selected pass-fail limit. Also, optionally, a chart recorder 38 may be associated with the apparatus 10 to make a chart record of the force-deflection curve.

Figure 2:
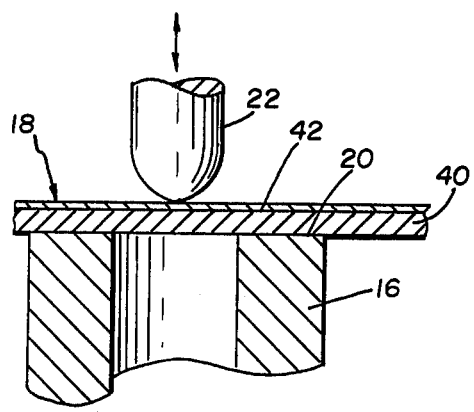
FIG. 2 is an enlarged partial cross section of the ring and plunger force-applying portion of the apparatus of FIG. 1.

As illustrated in the enlarged partial section of FIG. 2, the workpiece 18, which is the subject of the present testing method, comprises a substrate 40 which carries a coating 42 adhered thereto. One example of a typical workpiece 18 is that mentioned above, namely, a porcelain-on-steel printed circuit board. When the plunger 22 is forced downwardly against the coating, tensile and shear stresses are established in the coating. The present method measures the loading force and the deflection of whatever indentation is produced by the plunger 22 as the plunger 22 is pressed steadily against the workpiece with uniformly increasing force. We have found that the force-deflection curve is essentially linear before initial cracking of the coating 42 occurs. Thereafter, the slope of the force-deflection curve decreases abruptly during whatever additional deflection occurs after cracking has begun. The test is complete and is stopped when this change occurs. We have also found that in the case of porcelain-on-steel, a porcelain coating with poor adhesion will crack under a much smaller force than the force required to crack a workpiece having high adhesion, for the same amount of deflection.

Figure 3:
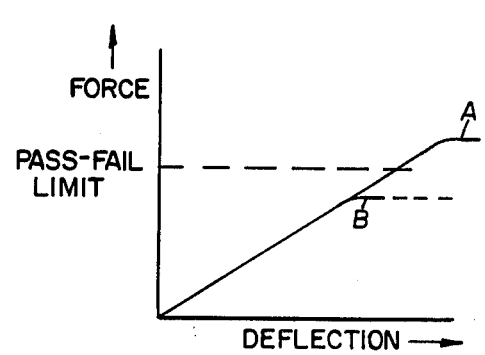
FIG. 3 is a curve of force versus deflection showing the limits of acceptable and nonacceptable samples as well as a pass-fail limit which can be utilized during manufacture.

A curve of force against deflection, which could be obtained from the chart recorder 38, is shown in FIG. 3. In this curve the linear increase in deflection with increasing force is shown. The abrupt decrease in force which is required to cause additional deflection for a highly adhesive sample is shown at the level A of the curve of FIG. 3. The force required to produce additional deflection for a poorly adhesive sample is shown at B. The range between A and B may be taken as the range between the best adhered and the worst adhered samples of a particular batch.

Once the initial determination of the levels of force A and B of FIG. 3 have been determined, an engineer can select a value of force and thereby establish a pass-fail limit. This pass-fail limit is shown in FIG. 3 at some force value intermediate between the values represented by the points A and B on the curve.

Once the value and the pass-fail limit has been established, operators of factory test equipment can be informed of this value and pass-fail testing can begin. The operator, or an automatic machine, can then test individual workpieces to determine whether they exceed the pass-fail limit. Those workpieces which do exceed the pass-fail limit can be passed on for further manufacturing production.

The present testing method can be used for nondestructive inspection testing directly on workpieces in a production environment. Preferably, the test is applied to a point on the workpiece which will not later be occupied by circuit components or termination connectors, in the case of a porcelain-on-steel printed circuit board. At such a location any small indentation which might result from the application of the present method will not adversely affect the printed circuit board.

The present method is not limited to the solid sections of a porcelain-on-steel printed circuit board, or even to a porcelain-on-steel printed circuit board. It is applicable wherever there is a relatively rigid coating which can accept and support tensile and shear stresses.

In the case of printed circuit boards of the porcelain-on-steel type, it is possible to measure the adhesion near holes or at other locations where the section is not homogenous. Accordingly, a very practical production test for the adhesion of coatings to their substrates is available according to the present method.

What is claimed is:

1. A method of testing the adhesion of a coating to a substrate comprising the steps of:
   supporting the substrate against motion in a given direction,
   biasing a force applying member against the coating, increasing the force,
   measuring the force and the deflection caused by the force-applying member, and
   terminating the test when the rate of deflection as a function of increasing force decreases.

2. A method of testing the adhesion of a coating as defined in claim 1 wherein the supporting step is carried out by disposing the workpiece to be tested on a ring-shaped support, and wherein the force applying member used in the biasing step is a plunger.

3. A method of testing the adhesion of a coating as defined in claim 2 further comprising:
   making a chart record of the force-deflection curve; and
   testing a plurality of coated substrates to determine maximum and minimum values of the coating adhesion.

* * * * *